United States Patent [19]

Imai et al.

[11] 4,438,288
[45] Mar. 20, 1984

[54] DEHYDROGENATION OF HYDROCARBONS WITH A HALOGEN CONTACTING STEP

[75] Inventors: Tamotsu Imai, Mt. Prospect, Ill.; Chi-Wen Hung, San Rafael, Calif.

[73] Assignee: UOP Inc., Des Plaines, Ill.

[21] Appl. No.: 496,146

[22] Filed: May 19, 1983

Related U.S. Application Data

[63] Continuation-in-part of Ser. No. 477,699, Mar. 22, 1983, which is a continuation-in-part of Ser. No. 326,969, Dec. 2, 1981, abandoned.

[51] Int. Cl.$^3$ ............................ C07C 5/23; B01J 37/22
[52] U.S. Cl. ...................................... 585/379; 502/36; 502/37; 585/444; 585/629; 585/659; 585/660
[58] Field of Search ............... 585/379, 444, 629, 659, 585/660; 502/36, 37

[56] References Cited

U.S. PATENT DOCUMENTS

| | | | |
|---|---|---|---|
| 3,647,680 | 3/1972 | Greenwood et al. | 208/65 |
| 3,652,231 | 3/1972 | Greenwood et al. | 23/288 |
| 3,978,150 | 8/1976 | McWilliams | 585/659 |
| 3,981,824 | 9/1976 | Greenwood et al. | 208/140 |
| 4,094,817 | 6/1978 | Olson et al. | 208/140 |

*Primary Examiner*—Curtis R. Davis
*Attorney, Agent, or Firm*—James R. Hoatson, Jr.; Kenneth J. Pedersen; William H. Page, II

[57] ABSTRACT

This invention relates to a new process for dehydrogenating hydrocarbons utilizing a catalyst comprising a platinum group component, an alkali or alkaline earth component and a porous support material. After the catalyst is used to dehydrogenate hydrocarbons it is contacted in a catalyst regeneration zone with a halogen component to produce a regenerated catalyst containing added halogen component, which regenerated catalyst can then be reused to dehydrogenate hydrocarbons. The added halogen component increases the catalyst's activity and stability in the dehydrogenation process.

13 Claims, No Drawings

DEHYDROGENATION OF HYDROCARBONS WITH A HALOGEN CONTACTING STEP

CROSS-REFERENCE TO RELATED APPLICATIONS

This application is a continuation-in-part of prior copending application Ser. No. 477,699 filed Mar. 22, 1983 which is a continuation-in-part of application Ser. No. 326,969 filed Dec. 2, 1981 and now abandoned.

BACKGROUND OF THE INVENTION (1) Field of the Invention

This invention pertains to the conversion of hydrocarbons especially the dehydrogenation of dehydrogenatable hydrocarbons, in the presence of a heterogeneous catalyst composite. Dehydrogenatable hydrocarbons contain at least two non-aromatic adjacent carbon atoms having one or two carbon-carbon bonds in common, each carbon atom of the pair having at least one hydrogen atom bonded to it. A heterogeneous catalyst is one which is in a phase different from the phase or phases of the reactants it catalyzes, for example, a solid catalyst which catalyzes liquid or gaseous reactants.

Dehydrogenating hydrocarbons is an important commercial process because of the great demand for dehydrogenated hydrocarbons especially olefins, as raw materials for the manufacture of various chemical products such as detergents, high octane gasolines, pharmaceuticals, plastics, synthetic rubbers, and other well-known products. In a commercial dehydrogenation process it is generally desired to dehydrogenate the hydrocarbon feedstock with little or no simultaneous cracking or isomerization of it. Preferably, the isomerization activity of dehydrogenation catalysts is maintained at less than 2 mol % of the feedstock, measured as the number of mols of isomerized hydrocarbons in the product relative to the feedstock. Preferably, the cracking activity of dehydrogenation catalysts is maintained at less than 10 mol % of the feedstock, measured as the number of mols of cracked hydrocarbons in the product relative to a feedstock of pure isobutane. One example of a dehydrogenation process is dehydrogenating isobutane to produce isobutylene which can be used to make, for example, tackifying agents for adhesives, viscosity-index additives for motor oils and impact-resistant and anti-oxidant additives for plastics.

(2) Description of the Prior Art

It is well known to catalyze the conversion of liquid or gaseous hydrocarbons with solid catalysts comprising platinum group metals. For example, U.S. Pat. Nos. 2,479,109 and 2,479,110 disclose a catalyst comprising platinum on alumina with combined halogen for catalyzing reforming, hydrogenating, hydrocracking, oxidizing and dehydrogenating reactions. The term "reforming" in these patents means simultaneously dehydrogenating, isomerizing, cyclizing and cracking a gasoline feedstock. The combined halogen component of this catalyst contributes to a controlled type of cracking activity. For reforming applications the halogen content is preferably maintained below about 8 weight % of the alumina to avoid excessive side reactions, including cracking reactions, which result in excessive gas formation and low liquid volume yield of reformed products.

U.S. Pat. No. 2,602,772 discloses converting hydrocarbons, especially reforming and hydrocracking hydrocarbons, with a catalyst comprising platinum, not more than 1 weight % of an oxide of an alkaline earth metal or magnesium and from about 0.1 to about 8 weight % combined halogen on alumina. According to this patent catalysts containing an alkaline earth metal or magnesium oxide produced less carbon, or coke, after 3 days of reforming operations. The halogen content for catalysts of this patent is from 0.3 to 3 weight %, preferably between 0.6 and 2.3 weight %.

U.S. Pat. No. 2,930,763 discloses a two-step process for reforming hydrocarbons. In the first step a hydrocarbon fraction containing unsaturated compounds and/or nitrogen, sulfur or oxygen compounds is contacted with hydrogen in the presence of a catalyst comprising platinum and an alkali metal component on alumina to hydrogenate and saturate the unsaturated compounds and/or reduce the nitrogen, sulfur or oxygen content of the hydrocarbon fraction. In the second step of this process the treated hydrocarbon fraction from the first step is contacted at reforming conditions with a conventional reforming catalyst comprising platinum and combined halogen on alumina. Optionally the catalyst utilized in the first step may contain halogen. A catalyst consisting essentially of alumina, from about 0.01% to about 1% by weight of platinum, from about 0.1% to about 1% by weight of combined halogen, and from about 0.01% to about 1% by weight of an alkali metal is recited in claim 2 of this patent.

U.S. Pat. No. 3,531,543 discloses dehydrogenating hydrocarbons with a catalyst comprising platinum, tin and neutralized metal oxide supports. The preferred supports are oxide materials whose intrinsic acidity is substantially reutralized by an alkali or alkaline earth metal component. Pure alumina, for example, has such intrinsic adicity. (cf. Pines and Haag, *Journal of the American Chemical Society*, 82,2471 (1960). Evidence of this acidity is that alumina catalyzes the skeletal isomerization of olefins, dehydrates alcohols and strongly chemisorbs amines. Also, with increasing amounts of alkali present there is a parallel decrease in these acidic alumina properties. Preferably the support of this patent is a non-acidic lithiated alumina. Perferably, the catalysts of this patent are prepared from halogen free compounds. Compounds containing halogen may be used provided halogen is efficiently removed from the catalyst.

U.S. Pat. No. 3,647,680 discloses a continuous moving bed reforming-regeneration process utilizing a catalyst comprising a platinum group metal, combined halogen and alumina. The catalyst may also include a promoter, such as rhenium, for example. The catalyst is continuously cycled between the reforming reactor section and catalyst regeneration section to maintain catalyst activity at a predetermined high level without the removal of any reactor from the process stream. The catalyst regeneration section includes a carbon burn-off zone, a chlorination zone and a drying zone. A catalyst reducing zone is located immediately upstream of the reforming reactor section. In the chlorination zone, the catalyst is contacted with about a 2:1 mol ratio of steam and chlorine.

U.S. Pat. No. 3,652,231 discloses a reforming catalyst regeneration apparatus suitable for use in the regeneration section of the process disclosed in U.S. Pat. No. 3,647,680 discussed above. This apparatus comprises a carbon burn-off section, a halogen section and a drying section.

U.S. Pat. No. 3,745,112 discloses a catalyst for reforming hydrocarbons with comprises a platinum group component, a tin component and a halogen component with a porous support material. This patent discloses also that a platinum-tin-alkali or alkaline earth composite is a particularly effective catalyst for dehydrogenating hydrocarbons. In the dehydrogenation catalyst of this patent the alkali or alkaline earth component is added and the amount of halogen, if not entirely eliminated, is minimized in order to minimize or neutralize, according to the understanding of the art, the acidic functions of the alumina and halogen components which tend to promote cracking and isomerization reactions.

U.S. Pat. No. 3,892,657 discloses that indium is a good promoter for platinum group-containing catalysts when the atomic ratio of indium to platinum is from about 0.1:1 to about 1:1. This patent discloses also that a Group IVA component selected from the group of germanium, tin, and lead can be added to the acidic form of the indium-containing catalysts for reforming applications. The acidic form of this catalyst, then, comprises a platinum group component, a Group IVA component, an indium component, a halogen component and a porous support material. The acidic catalyst contains up to about 3.5 weight % halogen for reforming applications and up to about 10 weight % halogen for isomerization and cracking applications. In the dehydrogenation catalyst of this patent the alkali or alkaline earth component is added, however, and the halogen content is maintained at the lowest possible value (about 0.1 weight %).

U.S. Pat. No. 3,909,451 discloses a new method for making a dehydrogenation catalyst comprising a platinum component, a tin component and an alkali or alkaline earth component. In Example V this patent discloses a platinum, tin and potassium composition comprising less than 0.2 wt. % combined chloride.

U.S. Pat. No. 3,978,150 discloses a continuous moving bed dehydrogenation-regeneration process utilizing, preferably, a catalyst comprising chromium, vanadium or molybdenum, such as alumina promoted with chromium oxide. The catalyst regeneration section in this process comprises a carbon burn-off zone and a catalyst reducing zone, which is preferably designed in accordance with the teachings of U.S. Pat. No. 3,652,231 discussed above, but without the halogenation zone.

U.S. Pat. Nos. 4,329,258 and 4,363,721 disclose a catalyst comprising a platinum group metal, tin, an alkali or alkaline earth metal and combined halogen with a refractory oxide-mineral support. The atomic ratio of alkali or alkaline earth metal to platinum group metal for catalysts of these patents is from 0.2 to 10. These patentees discovered that parts-per-million quantities of alkali or alkaline earth component added to catalysts containing a platinum group metal and tin helped increase the $C_{5+}$ yield in a reforming process.

British Patent 1 499 297 discloses a dehydrogenation catalyst comprising platinum, at least one of the elements gallium, indium and thallium, and an alkali metal, especially lithium or potassium, with alumina as the carrier material. The catalysts of this patent also contain halogen in an amount of from 0.01 to 0.1 weight %. The halogen content is purposely reduced to within this low weight % range in order to increase the selectivity and stability of the catalyst.

There is no prior art dehydrogenation process, then, wherein a used dehydrogenation catalyst comprising a platinum group component, an alkali or alkaline earth component and a porous support material is contacted in a catalyst regeneration zone with a halogen component to produce a regenerated catalyst containing added halogen component. Surprisingly, we have discovered that a regenerated dehydrogenation catalyst with added halogen component exhibits more activity and activity stability when it is reused to dehydrogenate hydrocarbons.

BRIEF SUMMARY OF THE INVENTION

Our invention relates to a new process for dehydrogenating hydrocarbons. The process utilizes a catalyst comprising a platinum group component and an alkali or alkaline earth component with a porous support material. The catalyst is particularly useful for dehydrogenating paraffins having from 2 to 5 or more carbon atoms to the corresponding mono-olefins or for dehydrogenating mono-olefins having 3 to 5 or more carbon atoms to the corresponding di-olefins. After the catalyst is used to dehydrogenate hydrocarbons it is contacted in a catalyst regeneration zone with a halogen component to produce a regenerated catalyst containing added halogen component, which regenerated catalyst can then be reused to dehydrogenate hydrocarbons.

DETAILED DESCRIPTION OF THE INVENTION

Heterogeneous catalysis practice, that is, catalyzing reactions of liquid or gaseous reactants with solid catalysts, is important to industry. For many years persons skilled in the art of hydrocarbon conversion, for example, have endeavored to discover and develop new hydrocarbon conversion catalysts with improved performance characteristics. Many of these persons are highly trained in one or more of a wide variety of disciplines including, for example, organic and inorganic chemistry, solid state and surface physics, ceramics, metallurgy and chemical engineering. Notwithstanding this high level of skill in the art, hydrocarbon conversion catalysis, like other fields of heterogeneous catalysis, continues to be "a vast and confusing field replete with an enormous quantity of perhaps significant but empirical facts intermixed with perhaps useful theories." (C. N. Satterfield, Heterogeneous Catalysis in Practice, preface (1980)).

Consequently, significant contributions to the art of heterogeneous hydrocarbon conversion catalysis have generally resulted from empirical discoveries and developments rather than from theoretical extrapolations.

Our contribution to this field of art is that we have discovered a new process for dehydrogenating hydrocarbons. The process utilizes a catalyst comprising a platinum group component and an alkali or alkaline earth component with a porous carrier material. The platinum group component is preferably present in the final composite in an amount, calculated on an elemental basis, of about 0.01 to 5 weight %; and the alkali or alkaline earth component is preferably present in an amount of about 0.01 to 15 weight %. Dehydrogenation conditions include a temperature of from about 750 to 1650° F., a pressure of from about 0.01 to 10 atmospheres and a liquid hourly space velocity (LHSV - calculated on the basis of the volume amount, as a liquid at standard conditions, of hydrocarbon charged to the dehydrogenation zone per hour divided by the volume of the catalyst bed utilized) of from about 0.1 to 100 hr.$^{-1}$. The hydrocarbons to be dehydrogenated are dehydrogenatable hydrocarbons including paraffins, alkylaromatics, naphthenes and olefins, having from 2 to 30 or more carbon atoms. One group of hydrocarbons which can be dehydrogenated with the catalyst is the group of normal paraffins having from 6 to 30 or more carbon atoms. The catalyst is particularly useful for dehydrogenating paraffins having from 2 to 5 or more carbon atoms to the corresponding mono-olefins or for dehydrogenating mono-olefins having 3 to 5 or more carbon atoms to the corresponding di-olefins.

To be commercially successful a dehydrogenation catalyst must satisfy three requirements, namely high activity, high selectivity and good stability. Activity is a measure of the catalyst's ability to help convert reactants into products at a specified severity level where severity level means the reaction conditions used - that is, the temperature, pressure, contact time and presence of diluents such as hydrogen, if any. For dehydrogenation catalyst activity we measured the conversion, or disappearance, of paraffins, in percent, from the feedstock. Selectivity is a measure of the catalyst's ability to help convert reactants into desired product or products relative to the amount of reactants charged or converted. For catalyst selectivity we measured the amount of olefins in the product, in mol percent, relative to the total mols of the paraffins converted. Stability is a measure of the rate of change with time of the activity and selectivity parameters - the smaller rate implying the more stable catalysts. The absolute value of the slope of the activity versus time curve is the activity stability, and the absolute value of the slope of the selectivity versus time curve is the selectivity stability.

Since dehydrogenation of hydrocarbons is an endothermic reaction and conversion levels are limited by chemical equilibrium, it is desirable in order to achieve high conversion to operate at high temperatures and low hydrogen partial pressures. At such severe conditions it is difficult to maintain high activity and selectivity for long periods of time because undesirable side reactions such as aromatization, cracking, isomerization and coke formation increase. Therefore, there is a considerable demand for a new hydrocarbon dehydrogenation process utilizing a catalyst with improved activity, selectivity and stability characteristics at these conditions. The process of our invention, that is, a dehydrogenation process utilizing a catalyst comprising a platinum group component, an alkali or alkaline earth component and a porous carrier material, will answer to such a demand when: (a) a dehydrogenatable hydrocarbon is contacted in a dehydrogenation zone with the catalyst to produce a dehydrogenated hydrocarbon and a used catalyst; (b) then, said used catalyst is contacted in a catalyst regeneration zone with a halogen component to produce a regenerated catalyst containing added halogen component; and (c) then a dehydrogenatable hydrocarbon is contacted in a dehydrogenation zone with said regenerated catalyst to produce a dehydrogenated hydrocarbon.

Regarding the platinum group component of our catalyst composite, it may be selected from the group of platinum or palladium or iridium or rhodium or osmium or ruthenium or mixtures thereof. Platinum, however, is the preferred platinum group component. We believe that substantially all of the platinum group component exists within the final catalyst in the elemental metallic state.

Preferably the platinum group component is well dispersed throughout the catalyst. The platinum group component generally will comprise about 0.01 to 5 weight %, calculated on an elemental basis, of the final catalyst. Preferably the catalyst comprises about 0.1 to 1 weight % platinum.

The platinum group component may be incorporated in the catalyst in any suitable manner such as, for example, by coprecipitation or cogelation, ion exchange or impregnation, or deposition from a vapor phase or from an atomic source or by like procedures either before, while or after other catalytic components are incorporated. The preferred method of incorporating the platinum group component is to impregnate the support material with a solution or suspension of a decomposable compound of a platinum group metal. For example, platinum may be added to the support by commingling the latter with an aqueous solution of chloroplatinic acid. Another acid, for example, nitric acid, or other optional components may be added to the impregnating solution to further assist in dispersing or fixing the platinum group component in the final catalyst.

Regarding the alkali or alkaline earth component of our catalyst, it is selected from the group of cesium, rubidium, potassium, sodium and lithium or from the group of barium, strontium, calcium and magnesium or mixtures of components from either or both of these groups. Lithium, sodium, potassium and magnesium, however, are the preferred alkali or alalkine earth components. We believe that the alkali or alkaline earth component exists in the final catalyst in an oxidation state above that of the elemental metal. The alkali or alkaline earth component may be present as a compound such as the oxide, for example, or combined with the carrier material or with the other catalytic components. Preferably the alkali or alkaline earth component is well dispersed throughout the catalyst. The alkali or alkaline earth component generally will comprise about 0.01 to 15 weight %, calculated on an elemental basis, of the final catalyst. Preferably the catalyst comprises about 1 to 3 weight % potassium.

The alkali or alkaline earth component may be incorporated in the catalyst in any suitable manner such as, for example, by coprecipitation or cogelation, by ion exchange or impregnation, or by like procedures either before, while or after other catalytic components are incorporated. We have obtained best results when potassium has been added to the carrier material from an impregnating solution of potassium nitrate.

The catalyst of our invention comprises an atomic ratio of alkali or alkaline earth component to platinum group component of more than 10. In prior art reforming or isomerization catalysts comprising a platinum group component and an alkali or alkaline earth component, on the other hand, the amount of the alkali or alkaline earth component was purposely maintained below this level. This is because addition of the alkali or alkaline earth component tends to decrease the acidity of these catalysts, which acidity is responsible for accelerating isomerization and cracking reactions. For reforming and isomerization catalysts it is desired to maintain some substantial amount of catalyst acidity, so the atomic ratio of alkali or alkaline earth component to platinum group component for these catalysts has been maintained at less than or equal to 10. For our catalyst, however, the atomic ratio of the alkali or alkaline earth component to the platinum group component is more than 10; preferably it is from about 15 to about 25.

The porous support material of the catalyst of our invention is preferably a porous, absorptive support with high surface area of from about 25 to 500 m²/g. The porous support material should be relatively refractory to the conditions utilized in the dehydrogenation process. It is intended to include within the scope of our invention the use of support materials which have traditionally been utilized in hydrocarbon conversion catalysts such as, for example; (1) activated carbon, coke, or charcoal; (2) silica or silica gel, silicon carbide, clays, and silicates including those synthetically prepared and naturally occurring, which may or may not be acid treated, for example, attapulgus clay, china clay, diatomaceous earth, fuller's earth, kaolin, kieselguhr, etc.; (3) ceramics, porcelain, crushed firebrick, bauxite; (4) refractory inorganic oxides such as alumina, titanium dioxide, zirconium dioxide, chromium oxide, beryllium oxide, vanadium oxide, cerium oxide, hafnium oxide, zinc oxide, magnesia, boria, thoria, silica-alumina, silica-magnesia, chromia-alumina, alumina-boria, silica-zirconia, etc.; (5) crystalline zeolitic silicates such as naturally occurring or synthetically prepared mordenite, faujasite and/or silicalite either in the hydrogen form or in a form which has been exchanged with metal cations; (6) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; and (7) combinations of materials from one or more of these groups. The preferred support material for our catalyst is alumina, especially gamma- or et-alumina.

The preferred alumina support material may be prepared in any suitable manner from synthetically prepared or naturally occurring raw materials. The support may be formed in any desired shape such as spheres, pills, cakes, extrudates, powders, granules, etc., and it may be utilized in any particle size. A preferred shape of alumina is the sphere. A preferred particle size is about 1/16 inch in diameter, though particles as small as about 1/32 inch, and smaller, may also be utilized.

To make alumina spheres aluminum is converted into an alumina sol by reacting it with a suitable peptizing acid and water, and then dropping a mixture of the resulting sol and a gelling agent such as hexamthylenetetramine into an oil bath to form spherical particles of an alumina gel which are easily converted into the gamma- or eta-alumina support material by known methods including aging, drying and calcining. To make alumina cylinders, an alumina powder is mixed with water and enough of a suitable peptizing agent such as nitric acid, for example, until an extrudable dough is formed. The dough is then extruded through a suitably-sized die and cut to form extrudate particles. Other shapes of the alumina support material may also be prepared by conventional methods. After the alumina particles are shaped generally they are dried and calcined. The alumina support carrier may be subjected to intermediate treatments during its preparation, including washing with water or contacting with ammonium hydroxide, for example, which treatments are generally well-known in the art.

The catalytic composite of our invention may also contain a halogen component. The halogen component may be either fluorine, chlorine, bromine or iodine or mixtures thereof. Chlorine and bromine are the preferred halogen components. The halogen component is generally present, we believe, in a combined state with the porous carrier material. Preferably the halogen component is well dispersed throughout the catalytic composite. Preferably the halogen component will comprise from more than 0.2 wt. % to about 15 wt. %, calculated on an elemental basis, of the final catalytic composite. Preferably the catalyst comprises about 1 to 3 wt. % chlorine.

The halogen component may be incorporated in the catalytic composite in any suitable manner, either during the preparation of the carrier material or before, while or after other catalytic components are incorporated. For example, the alumina hydrosol utilized to form the preferred aluminum carrier material may contain halogen and thus contribute at least some portion of the halogen content in the final catalyst composite. Also, the halogen component or a portion thereof may be added to the catalyst composite during the incorporation of the carrier material with other catalyst components, for example, when using chloroplatinic acid to impregnate the platinum component. Also, the halogen component or a portion thereof may be added to the catalyst composite by contacting the catalyst with the halogen or a compound, solution or dispersion containing the halogen before or after other catalyst components are incorporated with the carrier material. Suitable compounds containing the halogen include acids containing the halogen, for example, hydrochloric acid.

According to the process of our invention added halogen component is incorporated in the catalyst in catalyst regeneration zone by contacting the catalyst therein with a compound, solution or dispersion containing the halogen component. In the regeneration zone carbon deposited on the catalyst as coke during use of the catalyst in a dehydrogenation proces is burned off the catalyst and the platinum group component in the catalyst is reconditioned or redistributed to provide a regenerated catalyst with performance characteristics as good as those of the fresh or unused catalyst. Typically the coke is burned off the used catalyst by contacting it with a controlled amount of an oxygen-containing gas at an elevated temperature. For example, the used catalyst may be contacted at about 850° F. with a regeneration gas stream of nitrogen containing between about 0.3 and 0.8 mol % oxygen to burn the coke from it. This carbon burn step is continued until the exothermic heat of coke combustion has peaked and subsided or until the oxygen content of the effluent gas stream from the regeneration zone is the same as in the inlet stream. Typically the platinum group component in the used catalyst is reconditioned or redistributed by contacting it with a controlled amount of an oxygen-containing gas at an elevated temperature. For example, to redistribute the platinum group component the used catalyst may be contacted at about 950° F. with a regeneration gas stream of nitrogen containing about 5.0 mol % oxygen.

The catalyst may be contacted with the halogen component during the carbon burn step, or during the platinum group component redistribution step, or during both of these steps, or after either or both of these steps. For example, the used catalyst after the redistribution step may be contacted at about 950° F. with a regeneration gas stream of nitrogen containing enough hydrogen chloride gas to maintain more than about 50 ppm hydrogen chloride in the effluent gas stream from the regeneration zone. During this halogen contacting step the water level in the regeneration gas entering the regeneration zone is monitored and enough hydrogen chloride gas is added to maintain about a 20:1 mol ratio of water to chloride at the inlet to the regeneration zone. The redistribution and/or halogen contacting steps may be continued for a period of about 8 hours. In the regeneration zone, for the carbon burn step and/or the platinum group component redistribution step and/or the halogen contacting step, the catalyst particles may be in a fixed bed, a fluidized bed or moving bed like the one disclosed in U.S. Pat. No. 3,647,680.

The used dehydrogenation catalyst may be regenerated periodically; for example, a fixed bed reactor containing the catalyst may be shut down or taken off stream and the catalyst regenerated in situ. Or, the catalyst may be regenerated continuously; for example, used catalyst from a fluidized bed reactor or from a moving bed reactor may be removed from the reactor and transferred to a separate regeneration zone to be regenerated there while the reactor remains on stream.

Preferably the catalyst of our invention may also contain a Group IVA component. The Group IVA component may be selected from the group of germanium or tin or lead or mixtures thereof. Tin, however, is the preferred Group IVA component. We believe the Group IVA component exists within the catalyst in an oxidation state above that of the elemental metal. The Group IVA component may be present as a compound such as the oxide, for example, or combined with the carrier material or with the other catalytic components.

Preferably the Group IVA component is well dispersed throughout the catalyst. The Group IVA component generally wil comprise about 0.01 to 5 weight %, calculated on an elemental basis, of the final catalyst composite. Preferably the catalyst comprises about 0.2 to 2 weight % tin.

The Group IVA component may be incorporated in the catalytic composite in any suitable manner such as, for example, by coprecipitation or cogelation, ion exchange or impregnation or by like procedures either before, while or after other catalytic components are incorporated. A preferred method of incorporating the tin component is cogelling it during preparation of the porous carrier material. For example, tin may be incorporated in an alumina support material by mixing a soluble tin compound such as stannous or stannic chloride with an alumina hydrosol, adding a gelling agent such as hexamethylenetetramine and dropping the mixture into an oil bath to form spheres containing alumina and tin. A preferred method of incorporating the germanium component is to impregnate the support material with a solution or suspension of a decomposable compound of germanium such as germanium tetrachloride dissolved in an alcohol. Likewise, the lead component may be impregnated from a solution of lead nitrate in water.

Optionally the catalyst composite utilized in the process of our invention may also contain a sulfur component. Generally the sulfur component will comprise from about 0.01 to 10 wt. %, calculated on an elemental basis, of the final catalytic composite. The sulfur component may be incorporated into the catalytic composite in any suitable manner. Preferably sulfur or a compound containing sulfur such as hydrogen sulfide or a lower molecular weight mercaptan, for example, is contacted with the catalyst composite in the presence of hydrogen at a hydrogen to sulfur ratio of about 100 and a temperature of from about 50° to about 1000° F., preferably under water-free conditions, to incorporate the sulfur component.

Optionally, the catalyst may also contain other, additional components or mixtures thereof which act alone or in concert as catalyst modifiers to improve catalyst activity, selectivity or stability. Some well-known catalyst modifiers include antimony, arsenic, berylium, bismuth, cadmium, calcium, chromium, cobalt, copper, gallium, gold, indium, iron, lithium, manganese, molybdenum, nickel, rhenium, scandium, silver, tantalum, thallium, titanium, tungsten, uranium, zinc, and zirconium. These additional components may be added in any suitable manner to the carrier material during or after its preparation, or they may be added in any suitable manner to the catalytic composite either before, while or after other catalytic components are incorporated.

Preferably the catalyst composite of our invention is nonacidic. "Nonacidic" in this context means that the catalyst has very little skeletal isomerization activity, that is, the catalyst converts less than 10 mol % of 1-butene to isobutylene when tested at dehydrogenation conditions and, preferably, converts less than 1 mol %. The acidity of the catalyst can be decreased if necessary to make the catalyst nonacidic by increasing the amount of the alkali or alkaline earth component, or by treating the catalyst with steam to remove some of the halogen component.

After the catalyst components have been combined with the porous carrier material, the resulting catalyst composite will generally be dried at a temperature of from about 212° to about 610° F. for a period typically of about 1 to about 24 hours or more and thereafter calcined at a temperature of about 610° to about 1120° F. for a period of about 0.5 to about 10 or more hours. Finally the calcined catalyst composite is typically subjected to a reduction step before its use in the dehydrogenation process. This reduction step is effected at a temperature of about 450° to about 1200° F. for a period of about 0.5 to about 10 or more hours in a reducing environment like dry hydrogen, for example, the temperature and time being selected to be long and hot enough to reduce substantially all of the platinum group component to the elemental metallic state.

According to the process of our invention the dehydrogenatable hydrocarbons are contacted with the catalytic composite of our invention in a dehydrogenation zone maintained at dehydrogenation conditions. This contacting may be accomplished in a fixed catalyst bed system, a moving catalyst bed system, a fluidized bed system, etc., or in a batch-type operation. A fixed bed system is preferred. In this fixed bed system the hydrocarbon feed stream is preheated to the desired reaction temperature and then passed into the dehydrogenation zone containing a fixed bed of the catalyst. The dehydrogenation zone may itself comprise one or more separate reaction zones with heating means therebetween to insure that the desired reaction temperature can be maintained at the entrance to each reaction zone. The hydrocarbon may be contacted with the catalyst bed in either upward, downward or radial flow fashion. Radial flow of the hydrocarbon through the catalyst bed is preferred for commercial scale reactors. The hydrocarbon may be in the liquid phase, a mixed vapor-liquid phase or the vapor phase when it contacts the catalyst; preferably it is in the vapor phase.

Conditions in the dehydrogenation zone include a temperature of from about 750° to about 1650° F., a pressure of from about 0.01 to 10 atmospheres and a liquid hourly space velocity (LHSV) of from about 0.1 to 100 hr.$^{-1}$. Generally for normal paraffins the lower the molecular weight the higher the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen and the products of dehydrogenation reactions. This effluent stream is typically cooled and passed to a hydrogen separation zone to separate a hydrogen-rich vapor phase from a hydrocarbon-rich liquid phase. The hydrogen-rich vapor phase may be recycled to the dehydrogenation zone. Generally, the hydrocarbon-rich liquid phase is further separated by means of either a suitable selective adsorbent, a selective solvent, a selective reaction or reactions or by means of a suitable fractionation scheme. Unconverted dehydrogenation hydrocarbons are recovered and may be recycled to the dehydrogenation zone. Products of the dehydrogenation reactions are recovered as final products or as intermediate products in the preparation of other compounds.

The dehydrogenatable hydrocarbons may be admixed with a diluent material before, while or after being passed into the dehydrogenation zone. The diluent material may be hydrogen, steam, methane, ethane, carbon dioxide and the like. Hydrogen is the preferred diluent. Ordinarily, when hydrogen is utilized as the diluent it is utilized in amounts sufficient to insure a hydrogen to hydrocarbon mol ratio of about 0.1:1 to 40:1, with best results being obtained when the mol ratio range is about 1:1 to about 10:1. The diluent hydrogen stream passed to the dehydrogenation zone will typically be recycled hydrogen separated from the effluent from the dehydrogention zone in the hydrogen separation zone.

Water or a material which decomposes at dehydrogenation conditions to form water such as an alcohol, aldehyde, ether or ketone, for example, may be admixed with the dehydrogenatable hydrocarbons either continuously or intermittently, in an amount to provide, calculated on the basis of equivalent water, about 1 to about 20,000 wt. ppm of the hydrocarbon feed stream in the dehydrogenation zone. About 1 to 10,000 wt. ppm of water addition gives best results when dehydrogenating paraffins having from 6 to 30 more carbon atoms.

The following worked EXAMPLES are introduced to describe further the process of our invention and to teach one skilled in the art how to use it. These EXAMPLES represent one specific embodiment of our invention and are intended to be illustrative only and not restrictive.

EXAMPLE I

A catalyst "A" which comprised about 0.7 weight % platinum, about 0.5 weight % tin, about 3.0 weight % potassium and less than about 0.1 weight % chlorine and gamma alumina was prepared. To make the catalyst aluminum pellets were dissolved in a hydrochloric acid solution to form a sol and enough stannic chloride to provide about 0.5 weight % tin was added to the sol. Then hexamethylenetetramine was added to gel the sol and the mixture was dropped into an oil bath to form spherical particles having an average particle diameter of about 1/16 inch. Then, the spheres were aged in the oil bath, washed with an ammoniacal solution, dried and calcined to become gamma-alumina spheres containing about 0.5 weight % tin.

Then, the tin-containing alumina spheres were contacted with a deionized water solution containing chloroplatinic acid equivalent to the specified weight % of platinum and hydrochloric acid equivalent to 2 weight % of the alumina in a rotary drier for 15 minutes at room temperature. Then steam was passed to the jacket of the drier and the water was driven off under a nitrogen purge for 2-3 hours, leaving the platinum component and some chlorine component incorporated with the tin-containing alumina spheres. The chlorine component present was then removed by treating the platinum, tin and halogen-containing spheres at 1020° F. with 300 hr.$^{-1}$ GHSV of a 50/50 air/180° F. steam mixture for 6 hours. After this treatment with steam the spheres contained less than about 0.1 weight % chlorine. Then, the platinum and tin-containing spheres were contacted with a deionized water solution containing potassium nitrate equivalent to the specified weight % of potassium and dried to incorporate the potassium component. Then the platinum, tin and potassium-containing spheres were dried at 230° F. and 1000 hr.$^{-1}$ GHSV of dry air for ½ hour, the temperature was raised to 980° F., and the spheres were oxidized for about 3 hours. Finally, the spheres were reduced at 1160° F. in hydrogen gas at 700 hr.$^{-1}$ GHSV for 1 hour, and then sulfided at 1160° F. from a 1% mixture of hydrogen sulfide in hydrogen gas at 850 hr.$^{-1}$ GHSV for 1 hour. After the sulfiding step this catalyst comprised about 1 weight % sulfur, on an elemental basis.

Catalyst "A" was then then tested for dehydrogenation activity, selectivity and stability in a laboratory scale dehydrogenation plant comprising a reactor, a hydrogen separation zone, and heaters, coolers, pumps, compressors, and the like conventional equipment for handling hydrocarbons. In this plant, the feed stream containing the dehydrogenatable hydrocarbon is combined with a hydrogen gas stream and the resulting mixture is heated to the desired conversion temperature which is measured at the inlet to the dehydrogenation reactor. In the reactor the heated mixture contacts the fixed bed of catalyst in downflow fashion. The pressure reported herein is measured at the outlet from the reactor. An effluent stream is withdrawn from the reactor and cooled. A portion of the effluent stream is collected and analyzed to measure the amount of conversion, or activity, and the relative amount of desired dehydrogenated hydrocarbons, or selectivity, for the catalyst composite being tested. Conversion numbers reported herein are calculated on the basis of disappearance of isobutane, which was the feed stream, expressed in %. Similarly, selectivity numbers reported are calculated on the basis of desired isobutylene produced, expressed in mol %, of the isobutane converted.

Reaction conditions were; 1190° F., 2 atmospheres, 2 hydrogen to hydrocarbon mol ratio and 5.0 hr.$^{-1}$ LHSV. A summary of results from the test is presented in TABLE I.

EXAMPLE II

Used catalyst "A" from EXAMPLE I was used to prepare catalyst "B" for this EXAMPLE. Used catalyst "A" containing 5.6 weight % coke was contacted with about 2570 hr.$^{-1}$ GHSV of nitrogen containing 1.0 mol % oxygen at about 860° F. for 5 hours to burn coke from the catalyst and to decrease the coke level to less than 0.1 weight %. Then the used catalyst was contacted with about 2570 hr.$^{-1}$ GHSV of nitrogen containing 2.0 mol % oxygen at about the same temperature for 1 hour. Then, the used catalyst was contacted with about 2570 hr.$^{-1}$ GHSV of air at about 850° F. for 1 hour, and about 1500 hr.$^{-1}$ GHSV of dry air at about 950° F. for about 1 hour. Then about 0.9 hr.$^{-1}$ LHSV of 5.0 M hydrochloric acid solution and 36 hr.$^{-1}$ GHSV of chlorine gas were added to the flowing air stream for 2 hours. Finally, the catalyst was contacted with about 1500 hr.$^{-1}$ GHSV of dry air at about 950° F. for 0.5 hour and then cooled in the flowing air stream. After this regeneration the catalyst, now catalyst "B", contained about 1.9 weight %, on an elemental basis, of added chlorine component.

Catalyst "B" was then tested for isobutane dehydrogenation n the same manner as catalyst "A" above. A summary of results from the test is presented in TABLE I.

EXAMPLE III

Used catalyst "B" from EXAMPLE II was used to prepare catayst "C" for this EXAMPLE. Used catlayst "B" was contacted with about 2690 hr.$^{-1}$ GHSV of nitrogen and 1.0 mol % oxygen at about 860° F. for 2.5 hours to burn coke from it. Then the used catalyst was contacted with about 2690 hr.$^{-1}$ GHSV of nitrogen and 2.0 mol % oxygen at the same temperature for 2.5 hours. Then the used catalyst was contacted with about 2690 hr.$^{-1}$ of air at about 860° F. for 1.0 hour. In this EXAMPLE, no chlorine was added to catalyst "B" to make catalyst "C".

Catalyst "C" was then tested for isobutane dehydrogenation in the same manner as catalysts "A" and "B", above. A summary of results from the test is presented in TABLE I.

TABLE I

| Cata-lyst | Remarks | % Isobutane Conversion | | % change 20–90 hrs. |
|---|---|---|---|---|
| | | @ 20 hours | @ 90 hours | |
| A | fresh catalyst | 43.8 | 39.0 | 11 |
| B | carbon burn plus chlorine reconditioning | 44.5 | 42.2 | 5 |
| C | carbon burn only | 38.8 | 35.7 | 8 |

From TABLE I it is apparent that regenerated catalyst "B" with carbon burn and chlorine reconditioning according to the process of our invention exhibits higher early activity than both fresh catalyst "A" and regenerated catalyst "C" with carbon burn only, as represented by the higher % isobutane conversion for catalyst "B" at 20 hours of operation. Also, catalyst "B" of our invention exhibits higher stability than the other catalysts, as represented by the lower % change in isobutane conversion between 20 and 90 hours of operation for catalyst "B" than for catlaysts "A" and "C".

What we claim is:

1. A process for dehydrogenating hydrocarbons which comprises the steps of:
    (a) contacting a dehydrogenatable hydrocarbon in a dehydrogenation zone with a catalyst comprising a platinum group component, an alkali or alkaline earth component and a porous support material to produce a dehydrogenated hydrocarbon and a used catalyst;
    (b) contacting said used catalyst from step (a) above in a catalyst regeneration zone with a halogen component to produce a regenerated catalyst containing added halogen component; and
    (c) contacting a dehydrogenatable hydrocarbon in a dehydrogenation zone with said catalyst from step (b) above to produce a dehydrogenated hydrocarbon and a used catalyst.

2. The process of claim 1 wherein the catalyst in the dehydrogenation zone is nonacidic.

3. The process of claim 1 wherein the skeletal isomerization activity of the catalyst in the dehydrogenation zone is less than 10 mol. %.

4. The process of claim 1 wherein the atomic ratio of alkali or alkaline earth component to platinum group component of the catalyst is more than 10.

5. The process of claim 1 wherein the atomic ratio of alkali or alkaline earth component to platinum group component of the catalyst is from about 15 to about 25.

6. The process of claim 1 wherein the regeneration zone comprises a fixed bed of catalyst particles.

7. The process of claim 1 wherein the regeneration zone comprises a fluidized bed of catalyst particles.

8. The process of claim 1 wherein the regeneration zone comprises a moving bed of catalyst particles.

9. The process of claim 1 wherein the conditions in the dehydrogenation zone include temperature from about 750° to 1650° F., a pressure of from about 0.01 to 10 atmospheres, a LHSV of from about 0.1 to 100 hr.$^{-1}$ and a hydrogen to hydrocarbon mol ratio of about 0.1:1 to 40:1.

10. The process of claim 1 wherein the conditions in the catalyst regeneration zone include a carbon burn step at about 850° F. with a regeneration gas stream of nitrogen containing between about 0.3 and 0.8 mol % oxygen, a platinum redistribution step at about 950° F. with a regeneration gas stream of nitrogen containing about 5.0 mol % oxygen, a halogen contacting step at about 950° F. with a regeneration gas containing enough halogen to maintain more than about 50 ppm halogen in the effluent gas stream from the regeneration zone.

11. The process of claim 10 wherein enough hydrogen chloride gas is added to the regeneration zone to maintain about a 20:1 mol ratio of water to chloride in the regeneration zone.

12. A process for regenerating a dehydrogenation catalyst comprising a platinum group component, an alkali or alkaline earth component and a porous support material with comprises:
    (a) burning carbon from the used catalyst at about 850° F. with a regeneration gas stream containing between about 0.3 and 0.8 mol % oxygen, and
    (b) contacting the catalyst with a halogen component to provide a catalyst containing added halogen component.

13. The process of claim 12 which also comprises redistributing the platinum group component on the catalyst at about 950° F. with a regeneration gas stream containing about 5.0 mol % oxygen.

* * * * *